United States Patent [19]

Li et al.

[11] Patent Number: 6,150,554
[45] Date of Patent: Nov. 21, 2000

[54] OXIDATION PROCESS USING PERIODIC ACID

[75] Inventors: Jing Li, Edison; David M. Tschaen, Holmdel; Zhiguo Song; Mangzu Zhao, both of Edison, all of N.J.

[73] Assignee: Merck & Co., Inc., Rahway, N.J.

[21] Appl. No.: 09/283,563

[22] Filed: Apr. 1, 1999

Related U.S. Application Data

[60] Provisional application No. 60/081,273, Apr. 9, 1998.
[51] Int. Cl.[7] ............................. C07C 51/29; C07C 45/30
[52] U.S. Cl. ............................................. 562/419; 568/322
[58] Field of Search ................................ 562/419; 88/322

[56] References Cited

PUBLICATIONS

Zhao Tet Lett 39 5323, 1998.
Muzart, et al., Tetrahedron Letters, vol. 29(19), pp. 2321–2324, 1988.

*Primary Examiner*—Robert Gerstl
*Attorney, Agent, or Firm*—Valerie J. Camara; Mark R. Daniel

[57] ABSTRACT

The present invention relates to an oxidation which converts a primary or secondary alcohol of Formula II:

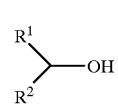

to an acid or ketone of Formula I:

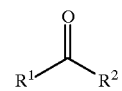

with periodic acid and a catalytic amount of a chromium reagent.

10 Claims, No Drawings

OXIDATION PROCESS USING PERIODIC ACID

This non-provisional application claims priority from provisional application U.S. S. No. 60/081,273, filed Apr. 9, 1998 (now abandoned).

BACKGROUND OF THE INVENTION

Oxidation is one of the most fundamental transformations in organic synthesis and there are numerous methods reported in the literature. (Hudlicky, M. "Oxidations in Organic Chemistry" ACS Monograph 186, 1990.) However, direct conversion of primary alcohols to the corresponding carboxylic acids is still a challenge especially in the presence of other functional groups. There are only a few commonly used methods for this transformation including $CrO_3/H_2SO_4$ (Bowden; Heilbron; Jones; Weedon *J. Chem. Soc.,* 1946, 39; Bowers; H.; Jones; L. *J. Chem. Soc.,* 1953, 2548; Millar, J. G.; Oehlschlager, A. C.; Wong, J. W. *J. Org. Chem.* 1983, 48, 4404.), $RuCl_3/H_5IO_6$(Carlsen, P. H. J.; Katsuki, T.; Martin V. S.; Sharpless, K. B. *J. Org. Chem.* 1981, 46, 3936.) and TEMPO/NaClO (Nooy, A. E. J. de; Besemer, A. C.; Bekkum, H. v. *Synthesis,* 1996, 1153.; Anelli, P. L.; Biffi, C.; Montanari, F.; Quici, S. *J. Org. Chem.* 1987, 52, 2559.; Miyazawa, T.; Endo, T.; Shiihashi, S.; Okawara, M. *J. Org. Chem.* 1985, 50, 1332). A two-step process involving Swern oxidation (Mancuso, A. J.; Huang, S-L., Swern, D. *J. Org. Chem.* 1978, 43, 2480.; Mancuso, A. J.; Brownfan, D. S.; Swern, D. *J. Org. Chem.* 1979, 44, 4148.; Ireland, R.; Norbeck, D. *J. Org. Chem.* 1985, 50, 2198.) followed by oxidation of the resulting aldehyde with $NaClO_2$ (Lindgren, B. O.; Nilsson, T. *Acta Chem. Scand.* 1973, 27, 888.; Dalcanale, E.; Montanari, F. *J. Org. Chem.* 1986, 51, 567) is another option. However, all of these procedures have limitations and disadvantages, and new methods for the oxidation of primary alcohols to the carboxylic acids are still desired. (Schroder, M.; Griffith, W. P. *J. Chem. Soc. Chem. Comm.* 1979, 58.; and Paquette, L. A.; Dressel, J.; Pansegrau, P. D. *Tetrahedron Lett.* 1987, 28, 4965. )

A very facile oxidation of primary alcohols to carboxylic acids using only catalytic $CrO_3$ and periodic acid ($H_5IO_6$) as the stoichiometric oxidant is described. Although chromium catalyzed oxidation of secondary alcohols is known, (Muzart, J. Chem. Review 1992, 92, 113–140; and Muzart, J. and Piva, O. Tetrahedron Lett. 1988, 29, 2321–2324.) a similar version for the oxidation of primary alcohols to the acids has not been reported. This chromium catalyzed oxidation method avoids the chromium disposal issues associated with running a typical Jones oxidation reaction, reduces the epimerization of any α-chiral centers, oxidizes secondary alcohols to the corresponding ketones in quantitative yield, and is a one step procedure. The reaction is mild, rapid, high yielding and only requires 1–2 mol % of $CrO_3$.

The present invention discloses a process for preparing a compound of Formula I:

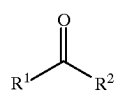

I comprising reacting a compound of Formula II,

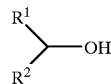

II in a solvent with periodic acid and a catalytic amount of a chromium reagent to oxide to the compound of Formula I.

SUMMARY OF THE INVENTION

The present invention discloses a process for preparing a compound of Formula I:

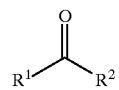

I wherein:

$R^1$ is:
a) OH,
b) H,
c) $C_1$–$C_8$ alkyl,
d) $C_1$–$C_8$ alkoxyl,
e) $C_3$–$C_7$ cycloalkyl,
f) aryl,
g) heteroaryl, or
h) heterocyclyl;

$C_1$–$C_8$ alkoxy, $C_1$–$C_8$ alkyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, aryl, heteroaryl, heterocyclyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_nCH_3$, $CO(CH_2)_nCH_2N(R^5)_2$, or when aryl is substituted on adjacent carbons they can form a 5- or 6-membered fused ring having one, two or three heteroatoms selected from O, N, and S, this ring is unsubstituted or substituted on carbon or nitrogen with one, two or three substituents selected from the group consisting of: OH, $CO_2R^4$, Br, Cl, F, I, $CF_3$, $N(R^7)_2$, $C_1$–$C_8$ alkoxy, $C_1$–$C_8$ alkyl, $C_3$–$C_8$ cycloalkyl, $CO(CH_2)_nCH_3$, and $CO(CH_2)_nCH_2N(R^5)_2$;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_nCH_3$, $CO(CH_2)_nCH_2N(R^5)_2$, and additionally the 5- or 6-membered aromatic ring can be benzofused and unsustituted or subtituted with one, two or three substituents as described above;

heterocyclyl is defined as a 5- or 6-membered, non-aromatic ring containing 1, 2 or 3 heteroatoms selected from O, N and S, which may contain one or two double bonds and which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_nCH_3$, $CO(CH_2)_nCH_2N(R^5)_2$, and additionally the 5- or 6-membered ring can be benzofused and unsustituted or subtituted with one, two or three substituents as described above;

$R^2$ is:
a) $C_1-C_8$ alkyl,
b) $C_3-C_7$ cycloalkyl,
c) aryl,
d) heteroaryl, or
e) heterocyclyl;
n is: 0 to 5;
t is: 0, 1 or 2;
$R^4$ is: H, or $C_1-C_8$ alkyl; or
$R^5$ is: H, or $C_1-C_8$ alkyl, or aryl;
$R^7$ is: H, $C_1-C_8$ alkyl, aryl, when two $R^7$ substutients are on the same nitrogen they can join to form a ring of 3 to 6 atoms;

comprising reacting a compound of Formula II in a solvent, wherein $R^1$ and $R^2$ substituents of Formula II are the same as $R^1$ and $R^2$ substituents defined in Formula I except that OH and $C_1-C_8$ alkoxyl substituents are not $R^1$ substituents of Formula II,

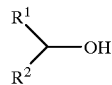

II with a solution of periodic acid, a catalytic amount of a chromium reagent in a solvent to oxidize to the compound of Formula I.

DETAILED DESCRIPTION OF THE INVENTION

The present invention discloses a process for preparing a compound of Formula I:

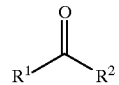

I wherein:
$R^1$ is:
a) OH,
b) H,
c) $C_1-C_8$ alkyl,
d) $C_1-C_8$ alkoxyl,
e) $C_3-C_7$ cycloalkyl,
f) aryl,
g) heteroaryl, or
h) heterocyclyl;
$C_1-C_8$ alkoxy, $C_1-C_8$ alkyl, or $C_3-C_8$ cycloalkyl, are unsubstituted or substituted with one, two or three substituents selected from the group consisting of: OH, $CO_2R^4$, Br, Cl, F, I, $CF_3$, $N(R^5)_2$, $C_1-C_8$ alkoxy, $C_3-C_8$ cycloalkyl, aryl, heteroaryl, heterocyclyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1-C_8$ alkoxy, $C_1-C_8$ alkyl, $C_3-C_8$ cycloalkyl, $CO(CH_2)_nCH_3$, $CO(CH_2)_nCH_2N(R^5)_2$, or when aryl is substituted on adjacent carbons they can form a 5- or 6-membered fused ring having one, two or three heteroatoms selected from O, N, and S, this ring is unsubstituted or substituted on carbon or nitrogen with one, two or three substituents selected from the group consisting of: OH, $CO_2R^4$, Br, Cl, F, I, $CF_3$, $N(R^7)_2$, $C_1-C_8$ alkoxy, $C_1-C_8$ alkyl, $C_3-C_8$ cycloalkyl, $CO(CH_2)_nCH_3$, and $CO(CH_2)_nCH_2N(R^5)_2$;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1-C_8$ alkoxy, $C_1-C_8$ alkyl, $C_3-C_8$ cycloalkyl, $CO(CH_2)_nCH_3$, $CO(CH_2)_nCH_2N(R^5)_2$, and additionally the 5- or 6-membered aromatic ring can be benzofused and unsustituted or subtituted with one, two or three substituents as described above;

heterocyclyl is defined as a 5- or 6-membered, non-aromatic ring containing 1, 2 or 3 heteroatoms selected from O, N and S, which may contain one or two double bonds and which is unsubstituted or substituted with one, two or three substituents selected from the group consisting of: OH, $CO_2R^4$, Br, Cl, F, I, $CF_3$, $N(R^5)_2$, $C_1-C_8$ alkoxy, $C_1-C_8$ alkyl, $C_3-C_8$ cycloalkyl, $CO(CH_2)_nCH_3$, $CO(CH_2)_nCH_2N(R^5)_2$, and additionally the 5- or 6-membered ring can be benzofused and unsubstituted or subtituted with one, two or three substituents as described above;

$R^2$ is:
a) $C_1-C_8$ alkyl,
b) $C_3-C_7$ cycloalkyl,
c) aryl,
d) heteroaryl, or
e) heterocyclyl;
n is: 0 to 5;
t is: 0, 1 or 2;
$R^4$ is: H, or $C_1-C_8$ alkyl; or
$R^5$ is: H, or $C_1-C_8$ alkyl, or aryl;
$R^7$ is: H, $C_1-C_8$ alkyl, aryl, when two $R^7$ substutients are on the same nitrogen they can join to form a ring of 3 to 6 atoms; comprising reacting a compound of Formula II in a solvent, wherein $R^1$ and $R^2$ substituents of Formula II are the same as $R^1$ and $R^2$ substituents defined in Formula I except that OH and $C_1-C_8$ alkoxyl substituents are not $R^1$ substituents of Formula II,

II with a solution of periodic acid, a catalytic amount of a chromium reagent in a solvent at a temperature range of about −20° C. to about 40° C. for about 15 minutes to about 24 hours to oxidize to the compound of Formula I.

The process as recited above, wherein the solvent is selected from the group consisting of: acetonitrile, tetrahydrofuran, diethyl ether, MTBE (methyl t-butyl ether), DME (dimethoxyethane), DIGLYME (2-methoxyethyl ether), TRIGLYME (triethylene glycol dimethyl ether), dioxane, or a mixture of said solvents, including a mixture of said solvents with water.

The process as recited above wherein the periodic acid ($H_5IO_6$) is utilized in about 2.0 to about 4.0 equivalents, preferably about 2.5 equivalents. A minimum of two equivalents of periodic acid are needed to carry out the oxidation from a primary alcohol to a carboxylic acid. Additionally, if the compound of Formula II contains any basic functional groups, an additional equivalent of periodic acid for each basic functional group will be needed to carry out the oxidation.

The process as recited above, wherein the chromium reagent is selected from the group consisting of: $CrO_3$, $Na_2Cr_2O_7$, $K_2Cr_2O_7$, $CrX_3$, where X is Cl, Br, F, $NO_2$, OAc, or $ClO_4$. The process as recited above, wherein the chromium reagent is utilized in about 0.1 to about 10 mole percent, preferably about 1.0 to about 2.0 mole percent.

The process as recited above, wherein the temperature range is about $-20°$ C. to about $30°$ C., and preferably about $-10°$ C. to about $0°$ C. The process as recited above, wherein the reaction time is about 15 minutes to about 24 hours and preferably between about 45 minutes and about 1.5 hours.

It is further understood that the substituents recited above would include the definitions recited below.

The alkyl substituents recited above denote straight and branched chain hydrocarbons of the length specified such as methyl, ethyl, isopropyl, isobutyl, tert-butyl, neopentyl, isopentyl, etc.

The alkenyl-substituents denote alkyl groups as described above which are modified so that each contains a carbon to carbon double bond such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclobutyl, cyclopentyl, cyclohexyl and 4-methylcyclohexyl.

The alkoxy substituent represents an alkyl group as described above attached through an oxygen bridge.

The aryl substituent represents phenyl and 1-naphthyl or 2-naphthyl, including aryl substituted with a 5- or 6-membered fused ring, such as an unsubstituted and substituted methylenedioxy, oxazolyl, imidazolyl, or thiazolyl ring.

The heteroaryl substituent represents a carbazolyl, furanyl, thienyl, pyrrolyl, imidazolyl, isoxazolyl, isothiazolyl, thiazolyl, oxazolyl, triazolyl, pyrazolyl, pyrazinyl, pyridyl, pyrimidyl, purinyl.

The heterocyclyl substituent represents, oxazolidinyl, thiazolidinyl, imidazolidinyl, thiazolidinyl, oxadiazolyl, thiadiazolyl, morpholinyl, piperidinyl, piperazinyl, or pyrrolidinyl.

Each of the above substituents (alkyl, alkenyl, alkynyl, alkoxy, cycloalkyl, aryl, heteroaryl, and heterocyclyl) can be either unsubstituted or substituted as defined within the description.

SCHEME I

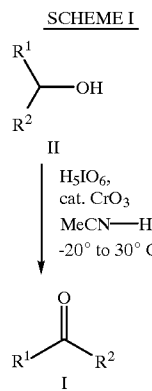

It has been found that some primary alcohols can be oxidized to the acids in aqueous acetonitrile (v/v~1/1) with $H_5IO_6$ and 5 mol % $CrO_3$. Conversions as high as 72% have been observed, but additional $H_5IO_6$ failed to push the reaction to completion. The reaction mixture also gradually turned greenish indicating generation of Cr(III) species that failed to turn over to Cr(VI). Nevertheless, these experiments proved that a catalytic process was viable. Since strong acids enhance the oxidation potential of $CrO_3$, $H_2SO_4$ was added to the reaction mixture. This appeared to improve the oxidation only slightly. On the other hand, water had a dramatic effect on the reaction rate. By eliminating the water from the system, complete reaction occurred in less than 15 minutes at r.t. Subsequently, we found that the presence of small amount of water attenuated the oxidation strength of the system and provided cleaner reactions. Thus, the best yields can be obtained by adding a solution of $H_5IO_6/CrO_{,3}$ (2.5 equiv./1.1 mol %) in wet MeCN (0. 75 v % water) to the alcohols at $0-5°$ C. The reactions were typically complete within one hour.

Results for the oxidation of a variety of alcohols as represented in the reaction scheme are summarized in Table 1.

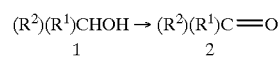

Oxidation of phenethanol (1a) gave phenylacetic acid (2a) in 96% yield (entry 1). Similarly, substrates with electron rich aromatic rings, such as 1b and 1c, were converted into the carboxylic acids 2b and 2c in excellent yields (entry 2,3). Most notably, chiral alcohol id was cleanly oxidized to 2d (95%) without any evidence of racemization based on chiral HPLC assay (entry 4). This was perhaps attributed to the fact that the aldehyde intermediate was very short lived under the reaction conditions. In all cases examined, the aldehyde intermediates were not observed in more than 5% during the reactions (HPLC). The cyclopropyl group in alcohol 1e was intact under the reaction conditions to give 2e in 90% yield (entry 5). Amidoacetal in 1f also survived to give the desired product 2f in 73% yield (entry 6). Cbz-protected amino alcohol 1g was oxidized to the Cbz-protected amino acid 2g in good yield without racemization (83%, entry 7). In this case, the reaction was carried out at r.t. due to the low solubility of the substrate at $0°$ C. For the vicinal diol, 1-phenyl-1,2-ethanediol (1h), carbon-carbon bond cleavage occurred to give benzoic acid in 77% yield (entry 8). To our surprise, oxidation of benzylic alcohols such as benzyl alcohol, 4-methoxybenzyl alcohol and furfuryl alcohol gave unsatisfactory results. Interestingly, electron deficient 4-nitrobenzyl alcohol (1i) gave a quantitative yield of 4-nitrobenzoic acid (entry 9). Substrates with very electron rich aromatic groups, such as 2,4,6-trimethoxybenzyl alcohol and 2-(3',4'-dimethoxyphenyl) ethanol, gave complex reaction mixtures. No reaction was observed for cinnamyl alcohol and 3-phenyl-2-propyn-1-ol. As expected, secondary alcohols, sec-phenethanol (1j) and 1-phenyl-2-propanol (1k), were oxidized to acetophenone and phenylacetone respectively in quantitative yield (entry 10, 11). Only 1.25 equivalents of periodic acid and 0.6 mol % $CrO_3$ were required in these cases.

TABLE 1

CrO₃ Catalyzed Oxidation of Alcohols

| Substrate | Temp/H₅IO₆/CrO₆ (C./equiv./mol %) | Product | Yield |
|---|---|---|---|
| Ph-CH₂CH₂-OH | 0/2.5/1.1 | Ph-CH₂-CO₂H | 96% |
| 2-methoxyphenethyl alcohol | 0/2.5/1.1 | 2-methoxyphenylacetic acid | 98% |
| 4-methoxyphenethyl alcohol | 0/2.5/1.1 | 4-methoxyphenylacetic acid | 92% |
| 2-Br-5-OMe-phenyl-CH₂-CH(Me)-CH₂OH | 0/2.5/1.1 | 2-Br-5-OMe-phenyl-CH₂-CH(Me)-CO₂H | 95% |
| Ph-C(cyclopropyl)-CH₂OH | 0/2.5/1.1 | Ph-C(cyclopropyl)-CO₂H | 90% |
| bicyclic oxazolidinone with CH₂OH | 0/2.5/1.1 | bicyclic oxazolidinone with CO₂H | 73% |
| Ph-CH₂-CH(NHCBZ)-CH₂OH | 0/2.5/1.1 | Ph-CH₂-CH(NHCBZ)-CO₂H | 83% |
| Ph-CH(OH)-CH₂OH | 0/3.5/1.6 | Ph-CO-OH | 77% |
| 4-O₂N-C₆H₄-CH₂OH | 0/2.5/1.1 | 4-O₂N-C₆H₄-CO₂H | 100% |
| Ph-CH(OH)-CH₃ | 0/1.25/0.6 | Ph-CO-CH₃ | 100% |
| Ph-CH₂-CH(OH)-CH₃ | 0/1.25/0.6 | Ph-CH₂-CO-CH₃ | 98% |

The present invention can be understood further by the following examples, which do not constitute a limitation of the invention.

General

All substrates were obtained commercially except 1d (preparation of this primary alcohol is described in Examples 2–5) and used without purification. The products were identified by comparing their $^1$H and $^{13}$C NMR spectra with those of commercial materials except 2d and 2f. The yields were determined by reverse phase HPLC with Zorbax SB-Phenyl or YMC ODS-AM columns and MeCN/0.1% $H_3PO_4$ as the mobile phase.

EXAMPLE 1

Oxidation of Primary Alcohol—Periodic Acid and Chromium Trioxide

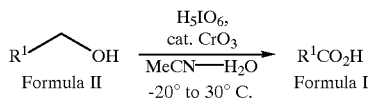

A stock solution of $H_5IO_6/CrO_3$ was prepared by dissolving $H_5IO_6$ (11.4 g, 50 mmol) and $CrO_3$ (23 mg, 1.2 mol %) in wet MeCN (0.75 v % water) to a volume of 114 mL (complete dissolution typically required 1–2 hours). The $H_5IO_6/CrO_3$ solution (11.4 mL) was then added to a solution of the alcohol 1 (2.0 mmol) in wet acetonitrile (10 mL, 0.75 v % water) in 30–60 minutes while maintaining the reaction temperature at 0–5° C. The mixture was aged at 0° C. for 0.5 h and the completion of the reaction was confirmed by HPLC assay. The reaction was quenched by adding an aqueous solution of $Na_2HPO_4$ (0.60 g in 10 mL $H_2O$). Toluene (15 mL) was added and organic layer was separated and washed with 1/1 brine/water mixture (2×10 mL) then a mixture of aqueous $NaHSO_3$ (0.22 in 5 mL water) and brine (5 mL). The organic layer was then concentrated to give the crude carboxylic acid 2. Most of the crude products were quite pure based on $^1$H NMR analysis and HPLC assay.

2g: The percent enantiomeric excess of Cbz-phenylalanine (2g) was measured by HPLC after removal of the Cbz-protecting group ($H_2$/Pd in MeOH). HPLC conditions: CROWNPAK CR(+) column; pH=2.0 aqueous $HClO_4$ mobile phase (0.80 mL/min); UV detection at 220 nm; Retention times: D-phenylalanine, 9.3 min; L-phenylalanine, 11.6 min.

2f: $^1$H NMR (CDCl$_3$) δ: 9.0–8.0 (broad, 1H), 7.47–7.30 (m, 5H), 5.71 (d, J=7.7 Hz, 1H), 4.43 (d, J=7.7 Hz, 1H), 2.70–2.40 (m, 2H), 2.33–2.27 (m, 1H), 2.17–1.80 (m, 3H), 1.58 (s, 3H).

$^{13}$C NMR (CDCl$_3$) δ: 172.04, 169.48, 137.52, 128.73, 126.16, 94.66, 77.05, 64.34, 34.52, 29.91, 23.45, 17.28.

EXAMPLE 2

Preparation of 2-bromo-5-methoxybenzyl alcohol

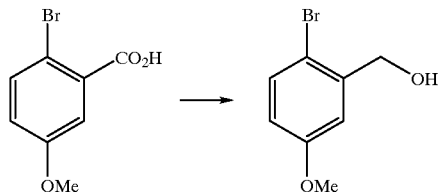

Sodium borohydride (8.6 g) is slurried in THF (150 mL KF=150 μg/mL) in a round bottom flask equipped with a thermocouple, an addition funnel, a nitrogen inlet a mechanical stirrer and a cooling bath. 2-Bromo-5-methoxybenzoic acid (50 g) is dissolved in THF (100 mL KF=150 μg/mL) is added to the sodium borohydride slurry over 45 min while maintaining the temperature at 20–25° C. The reaction must be controlled with intermittent cooling and by careful monitoring of the addition rate. The mixture is aged for 30 min at 20–25° C. Boron trifluoride etherate (36.9 g) is added over a period of 30 min at 30–35° C.

The addition of boron trifluoride etherate produces a delayed exotherm and should be added slowly in order to control the reaction temperature. The resulting white slurry is aged for 1 h at 30–35° C. and then sampled for HPLC assay. A peak at RT=8.7 min is an impurity related to the starting material. The acid is at RT=9.1 min.

The reaction mixture is cooled to 15° C. and carefully quenched into a cold (10° C.) saturated ammonium chloride solution (150 mL) while maintaining the temperature <25° C.

Ethyl acetate (500 mL) is added and the layers are separated. The organic layer is washed with water (100 mL) and then transferred to a 1 L round bottom flask equipped for distillation. The solution was concentrated and charged with fresh ethyl acetate. This is repeated until a solution with a volume of 200 mL has KF<200 μg/mL. The solvent is then switched to DMF to give the final volume of 200 mL with a KF<200 μg/mL.

EXAMPLE 3

Preparation of 2-bromo-5-methoxybenzyl chloride

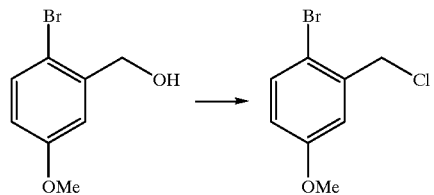

The DMF solution of the benzyl alcohol (91.3 g in 400 mL KF=300 μg/mL) is charged to a 2 L flask equipped with a mechanical stirrer, thermocouple, $N_2$ inlet, and cooling bath. The solution is cooled to 0–5° C. and the addition funnel is charged with thionyl chloride (55.0 g). The thionyl chloride is added over a period of 45 min while maintaining the temperture 5–10° C. The mixture is aged for 1 h at 5° C. and assayed by HPLC.

The addition funnel is charged with water (400 mL) which is added dropwise to the reaction mixture over a period of 30 min. while maintaining the temperture <15° C. The temperature is controlled by cooling and monitoring the rate of addition. The initial addition of water is highly exothermic. Using large excess of thionyl chloride results in a more exothermic quench. If the quench temperture is not controlled, hydrolysis of the benzyl chloride back to the alcohol may result.

The resulting thick white slurry is aged for 1 h at 0–5° C. The benzyl chloride is isolated by filtration. The cake is washed with (1:1) DMF:$H_2O$ (100 mL) and then water (200 mL). The solid is dried in vacuo to give 93 g of the benzyl chloride (94% yield, 96 A %).

HPLC assay: Column: Waters Symmetry C8, 4.6×250 mm; UV Detection: 220 nm; Column Temp: 25° C.; Flow rate: 1 mL/min.; Eluent: $CH_3CN$:$H_2O$:0.1% $H_3PO_4$ (70:30); RT (benzyl alcohol)=3.9 min; RT (benzyl chloride)=7.3 min.; and RT (DMF)=2.6 min.

EXAMPLE 4

Preparation of the Acetonide of N-propanoyl (1R, 2S)-cis-aminoindanol

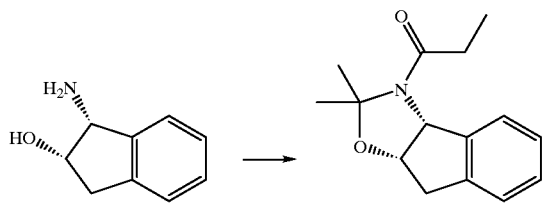

A 5 L 3-neck round bottom flask equipped with a mechanical stirrer, $N_2$ inlet, thermocouple probe, heating mantle, and addition funnel is charged with (1R,2S)-cis-aminoindanol (100 g), tetrahydrofuran (1.2 L, KF 120 mg/mL), and triethylamine (96 mL, KF 500 µg/mL). The resulting slurry is heated under a $N_2$ atmosphere to 40–45° C. giving a yellow solution. Propionyl chloride (59 mL) is charged to an addition funnel and added to the solution while maintaining the temperature at 45–50° C.

The temperature is controlled by rate of propionyl chloride addition and a cooling bath. HPLC assay shows >99% amide formed. Methanesulfonic acid (3 mL) is added to the reaction slurry. 2-Methoxypropene (140 mL) is charged to an addition funnel and added over 30 minutes at a temperature of 50° C.

The addition of 2-methoxypropene is mildly exothermic. The temperature is maintained by the rate of addition and a heating mantle. The reaction remains a slurry but does become less thick.

The reaction slurry is aged for 1–2 hours at 50° C. HPLC assay at this point shows <0.5A % of the amide remaining. The amide is not removed in the isolation so it is important to push the reaction to completion. The reaction slurry is cooled to 0–5° C. and quenched by addition of 5% aqueous sodium carbonate solution (1 L) and heptane (1 L). The layers are stirred and separated and the organic is washed with water (300 mL).

HPLC assay at this point shows the acetonide in >98A % and >90% yield. The acetonide/THF/heptane solution is filtered into a 2 L round bottom flask and the solution is distilled to a final volume of 700 mL. Heptane (1 L) is added and the solution is distilled to a final volume of 700 mL. The distillation is done under partial vacuum at ~50° C. NMR assay at this point shows <2 mol % THF. The solution is allowed to cool and is seeded with acetonide at 35–40° C. The thick slurry is aged for 1 hour at ambient temperature then cooled to 0–5° C. and aged for 1 hour. The slurry is filtered and the cake is washed with cold heptane (200 mL) and air dried to yield acetonide as a crystalline white solid (141.1 g, 85% yield, 99.6 A %).

EXAMPLE 5

Alkylation of the Acetonide with 2-bromo-5-methoxybenzyl chloride

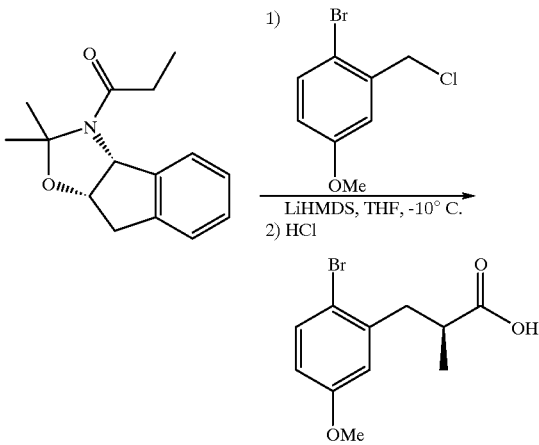

A THF solution (2L, KF<200 µg/mL) of the acetonide (252 g) and the benzyl chloride (255 g) is cooled to −10° C. Lithium bis(trimethylsilyl)amide (1.45 L) is added dropwise over 5 h at 0–2° C. The mixture is then aged for 1.5 h and assayed by HPLC.

The reaction is quenched by adding aqueous saturated ammonium chloride solution (1 L). The initial addition of the ammonium chloride should be slow in order to control the foaming. The rate can be increased when the foaming subsides.

The quenched reaction is then transfered into a mixture of aqueous ammonium chloride (1.5 L), water (0.5 L), and ethyl acetate (3 L). The mixture is then agitated for 15 min and the layers are separated. The organic layer is washed with water (1 L) and brine (0.5 L). The ethyl acetate solution is concentrated to a low volume and solvent switched to 1,4-dioxane. The dioxane solution is adjusted to a final volume of 1.8 L.

The dioxane solution of the coupled product is charged to a 12 L round bottom flask and 6 M HCl (1.5 L) is charged. The mixture is heated to reflux and monitored by HPLC.

The mixture is cooled to 20° C. and MTBE (3 L) is added. The mixture is agitated for 15 min and the layers are separated. The organic layer is washed with water (1 L). The MTBE solution of the crude acid is extracted with 0.6 M sodium hydroxide (2 L). The aqueous solution of the sodium salt of the acid is combined with MTBE (2.5 L) and cooled to 10° C.

The two phase mixture is acidified with 5.4 M sulfuric acid (250 mL), agitated for 15 min, settled and the layers separated. The MTBE solution of the acid is washed with water (0.5 L). The MTBE solution of the acid is dried by distillation and then solvent switched to THF. The final volume of the THF is 2 L with a KF<250 µg/mL.

HPLC assay: column: Waters Symmetry; Eluent: acetonitrile: water: phosphoric acid (70:30:0.1); Flow rate: 1 mL/min.; RT (acetonide)=4.5 min.; RT (benzyl chloride)= 7.5 min.; RT (coupled product)=11.5 min.; RT (aminondanol)=1.7 min.; RT (hydroxyamide)=1.7 min.; and RT (acid)=4.5 min.

EXAMPLE 6

Preparation of 3-(2-bromo-5-methoxyphenyl)-2-methylpropanol

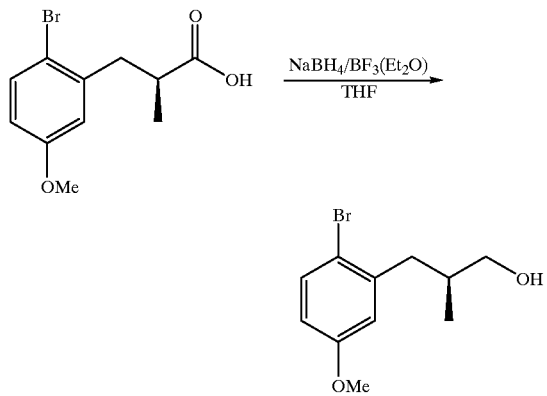

Sodium borohydride (33 g) is slurried in THF (0.5 L KF=200 μg/mL) in a round bottom flask. The THF solution (2 L) of the acid is added to the sodium borohydride slurry over 1 h while maintaining the temperature at 20–25° C.

The reaction is controlled with a cooling bath and by carefully monitoring the addition rate. A nitrogen sweep and proper venting of the hydrogen is also important.

The mixture is aged for 30 min at 20–25° C. Boron trifluoride etherate (152 g) is added over 1 h at 30–35° C. The addition produces a delayed exotherm and should be carefully monitored in order to control the reaction temperature. The resulting milky white slurry is aged for 1 h at 30° C. and sampled for HPLC assay.

The reaction mixture is cooled to 15° C. and carefully quenched in a cold (10° C.) ammonium chloride solution (1.5 L) while maintaining the temperature at 25° C. The rate of hydrogen evolution is controlled by the rate of the addition of the mixture into the ammonium chloride. The quenched mixture is distilled in vacuo to remove the THF. The aqueous layer is extracted with MTBE (1.5 L) and the organic layer is dried by flushing with additional MTBE. The MTBE solution is then solvent switched to hexanes and adjusted to a volume of 350 mL and seeded. The slurry is aged for 2 h at 20° C. and then cooled to 0–5° C. aged for 1 h and filtered. The cake is washed with cold hexanes (200 mL). The solid is dried under a nitrogen sweep. The isolated solid (164 g) is >99A % by HPLC and >99% ee.

HPLC: Column: Waters Symmetry C8; Solvent: acetonitrile:water: phosphoric acid (50:50:0.1); Flow rate: 1 mL/min.; Detection: 220 nm; RT (acid)=10.2 min.; RT (alcohol)=10.7 min.

Chiral HPLC: Column: Chiracel OD-H; Hexane:2-propanol (97:3); Flow rate: 1 mL/min.; Detection: 220 nm; RT minor isomer=21 min.; and RT major isomer=23 min.

EXAMPLE 7

Preparation of 3-(2-bromo-5-methoxyphenyl)-2-methylpropanol

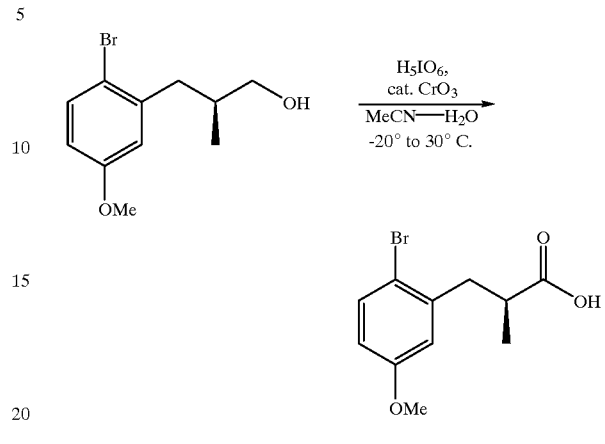

The alcohol was prepared following the general procedure recited in Example 1. The enantiomeric purity of product (2d) was determined by chiral HPLC after reducing it to the alcohol (1d) with $BH_3THF$. HPLC conditions: column CHIRALCEL OD-H; hexane/i-PrOH (97/3, 1.00 mL/min); UV detection at 220 nm. Retention times: (R)-isomer, 23.6 min; (S)-isomer, 29.2 min.

2d: $^1H$ NMR ($CDCl_3$) δ: 7.44 (d, J=8.7 Hz, 1H), 6.78 (d, J=3.1 Hz, 1H), 6.66 (dd, J=8.7, 3.1 Hz, 1H), 3.75 (s, 3H), 3.13 (dd, J=13.1, 6.8 Hz, 1H), 2.98–2.84 (m, 1H), 2.77 (dd, J=13.1, 7.4 Hz, 1H), 1.23 (d, J=6.9 Hz, 3H).

What is claimed is:

1. A process for preparing a compound of Formula I:

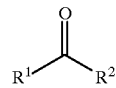

wherein:
$R^1$ is:
a) OH,
b) $C_1$–$C_8$ alkyl,
c) $C_1$–$C_8$ alkoxyl,
d) $C_3$–$C_7$ cycloalkyl,
e) aryl,
f) heteroaryl, or
g) heterocyclyl;

$C_1$–$C_8$ alkoxy, $C_1$–$C_8$ alkyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, aryl, heteroaryl, heterocyclyl, $CO(CH_2)_nCH_3$, and $CO(CH_2)_nCH_2N(R^5)_2$;

aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_nCH_3$, and $CO(CH_2)_nCH_2N(R^5)_2$, or when aryl is substituted on adjacent carbons they can form a 5- or 6-membered fused ring having one, two or three heteroatoms selected from O, N, and S, this ring is unsubstituted or substituted on carbon or nitrogen with one, two or three substituents selected from the group consisting of: OH, $CO_2R^4$, Br, Cl, F, I, $CF_3$, $N(R^7)_2$, $C_1$–$C_8$ alkoxy, $C_1$–$C_8$ alkyl, $C_3$–$C_8$ cycloalkyl, $CO(CH_2)_nCH_3$, and $CO(CH_2)_nCH_2N(R^5)_2$;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_nCH_3$, and $CO(CH_2)_nCH_2N(R^5)_2$, and additionally the 5- or 6-membered aromatic ring can be benzofused and unsubstituted or substituted with one, two or three substituents as described above;

heterocyclyl is defined as a 5- or 6-membered, non-aromatic ring containing 1, 2 or 3 heteroatoms selected from O, N and S, which may contain one or two double bonds and which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_nCH_3$, and $CO(CH_2)_nCH_2N(R^5)_2$, and additionally the 5- or 6-membered ring can be benzofused and unsubstituted or substituted with one, two or three substituents as described above;

$R^2$ is:
a) $C_1$–$C_8$ alkyl,
b) $C_3$–$C_7$ cycloalkyl,
c) aryl,
d) heteroaryl, or
e) heterocyclyl;

n is: 0 to 5;

t is: 0, 1 or 2;

$R^4$ is: H, or $C_1$–$C_8$ alkyl; or $R^5$ is: H, or $C_1$–$C_8$ alkyl, or aryl;

$R^7$ is: H, $C_1$–$C_8$ alkyl, aryl, when two $R^7$ substituents are on the same nitrogen they can join to form a ring of 3 to 6 atoms;

comprising reacting a compound of Formula II in a solvent, wherein $R^1$ and $R^2$ substituents of Formula II are the same as $R^1$ and $R^2$ substituents defined in Formula I except that OH and $C_1$–$C_8$ alkoxyl substituents are not $R^1$ substituents of Formula II,

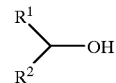

II with a solution of periodic acid, a catalytic amount of a chromium reagent in a solvent at a temperature range of about –20° C. to about 40° C. for about 15 minutes to about 24 hours to oxidize to the compound of Formula I.

2. The process as recited in claim 1, wherein the solvent is selected from the group consisting of: acetonitrile, tetrahydrofuran, diethyl ether, MTBE (methyl t-butyl ether), DME (dimethoxyethane), DIGLYME (2-methoxyethyl ether), TRIGLYME (triethylene glycol dimethyl ether), dioxane, and a mixture of said solvents, including a mixture of said solvents with water.

3. The process as recited in claim 2, wherein the periodic acid ($H_5IO_6$) is utilized in about 2.0 to about 4.0 equivalents.

4. The process as recited in claim 3, wherein the chromium reagent is selected from the group consisting of: $CrO_3$, $Na_2Cr_2O_7$, $K_2Cr_2O_7$, and $CrX_3$, where X is Cl, Br, F, $NO_2$, OAc, or $ClO_4$.

5. The process as recited in claim 4, wherein the chromium reagent is utilized in about 0.1 to about 10 mole percent.

6. The process as recited in claim 5, wherein the temperature range is about –10° C. to about 30° C.

7. The process as recited in claim 6, wherein the periodic acid ($H_5IO_6$) is utilized in about 2.5 equivalents.

8. The process as recited in claim 7, wherein the chromium trioxide ($CrO_3$) is utilized in about 1.0 to about 2.0 mole percent.

9. The process as recited claim 8, wherein the temperature range is about –10° C. to about 0° C.

10. The process as recited in claim 9, wherein the reaction time is about 45 minutes to about 1.5 hours.

* * * * *